US008617597B2

(12) United States Patent
King

(10) Patent No.: US 8,617,597 B2
(45) Date of Patent: Dec. 31, 2013

(54) PHARMACEUTICAL COMPOSITION CONTAINING A TETRAHYDROFOLIC ACID

(75) Inventor: Kristina King, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 949 days.

(21) Appl. No.: 11/773,689

(22) Filed: Jul. 5, 2007

(65) Prior Publication Data
US 2008/0038343 A1 Feb. 14, 2008

Related U.S. Application Data

(60) Provisional application No. 60/818,512, filed on Jul. 6, 2006.

(51) Int. Cl.
A61K 31/56 (2006.01)
A61K 31/4985 (2006.01)
A61K 9/16 (2006.01)
A61K 9/28 (2006.01)
A61P 15/00 (2006.01)

(52) U.S. Cl.
USPC .......................... 424/465; 424/451; 424/489

(58) Field of Classification Search
USPC .................................. 424/451, 464; 554/258
See application file for complete search history.

(56) References Cited

U.S. PATENT DOCUMENTS

| 4,292,315 | A | | 9/1981 | Vorys |
| 5,798,338 | A | | 8/1998 | Backensfeld et al. |
| 5,858,405 | A | * | 1/1999 | Gast .............................. 424/464 |
| 5,916,593 | A | | 6/1999 | De Haan et al. |
| 6,011,040 | A | | 1/2000 | Muller et al. |
| 6,190,693 | B1 | | 2/2001 | Kafrissen et al. |
| 6,441,168 | B1 | | 8/2002 | Muller et al. |
| 6,610,670 | B2 | | 8/2003 | Backensfeld et al. |
| 6,673,831 | B1 | | 1/2004 | Tobert |
| 2003/0119798 | A1 | | 6/2003 | Heil et al. |
| 2005/0227952 | A1 | | 10/2005 | Boissonneault |
| 2007/0093451 | A1 | | 4/2007 | Backensfeld et al. |
| 2008/0160004 | A1 | | 7/2008 | Strothmann et al. |

FOREIGN PATENT DOCUMENTS

| EP | 0253607 | | 4/1992 |
| EP | 0 330 284 | B1 | 7/1994 |
| EP | 1 353 700 | | 10/2003 |
| EP | 1214076 | * | 11/2003 |
| EP | 1257280 | | 10/2005 |
| EP | 1 353 700 | B1 | 11/2005 |
| EP | 1 634 586 | | 3/2006 |
| EP | 1632237 | A | 3/2006 |
| WO | WO 94/04157 | | 3/1994 |
| WO | WO 96/24337 | A1 | 8/1996 |
| WO | WO 97/41868 | | 11/1997 |
| WO | WO 98/01114 | A1 | 1/1998 |
| WO | WO 98/04246 | | 2/1998 |
| WO | WO 98/04267 | | 2/1998 |
| WO | WO 99/53910 | A | 10/1999 |
| WO | WO 01/15701 | A | 3/2001 |
| WO | WO-02 49675 | | 6/2002 |
| WO | WO 02/49675 | A1 | 6/2002 |
| WO | WO 02/055086 | | 7/2002 |
| WO | WO 03/070255 | A | 8/2003 |
| WO | WO 03/084547 | | 10/2003 |
| WO | WO 2004/019954 | | 3/2004 |
| WO | WO 2004/091535 | | 10/2004 |
| WO | WO-2006 120035 | | 11/2006 |
| WO | WO 2006/120035 | A2 | 11/2006 |
| WO | WO 2008/003363 | A1 | 1/2008 |
| WO | WO 2008/122439 | A3 | 10/2008 |

OTHER PUBLICATIONS

Anton et al., "Opinion of the Scientific Panel on Food Additives, Flavorings, Processing Aids and Materials in Contact with Food on a request from the Commissin related to Calcium L-Methylfolate." The EFSA Journal 2004:135;1-20.*
Suzuki et al., "Effect of crystallinity of microcrystalline cellulose on the compactability and dissolution of tablets." European Journal of Pharmaceutics and Biopharmaceutics 1999:47;225-230.*
Ardizzone et al., "Microcrystalline cellulose powders: structure, surface features and water sorption capability." Cellulose 1999:6;57-69.*
Remington's Pharmaceutical Sciences, Eighteenth Edition—1990, published by the Philadelphia College of Pharmacy and Science, "Oral Dosage Forms," 4 pages.
Materials Safety Data Sheet, Avicel® PH Microcrystalline Cellulose, FMC BioPolymer, MSDS Ref. No. 9004-34-6, Date Approved: Jan. 31, 2008, Revision No. 9, 2 pages.
Streiff, R.R., "Folate deficiency and oral contraceptives," J Am Medical Assoc., Oct. 5, 1970, 214(1): 105-108 (Abstract).
Durand, P., et al, "Folate deficiencies and cardiovascular pathologies," Clin Chem Lab Med, Jun. 1998, 36(7), 419-29 (Abstract).
Green, D., "Thrombophilia and stroke," Top Stroke Rehabil., 2003 Fall, 10(3): 21-33 (Abstract).
Eichholzer, M., et al, "Folate and the risk of colorectal, breast and cervix cancer: the epidemiological evidence", Swiss Med Wkly, 2001, 131: 539-549.
The Merk Index. An encyclopaedia of chemicals, drugs and biologicals. Fourteenth Edition, 2006. p. 1159 (Norgestrel).
The Merk Index. An encyclopaedia of chemicals, drugs and biologicals. Fourteenth Edition, 2006. p. 527 (Dienogest).
The Merk Index. An encyclopaedia of chemicals, drugs and biologicals. Fourteenth Edition, 2006. p. 466 (Ciproterona).
The Merk Index. An encyclopaedia of chemicals, drugs and biologicals. Fourteenth Edition, 2006. p. 635 (Estradiol).

(Continued)

Primary Examiner — Walter Webb
(74) Attorney, Agent, or Firm — Millen, White, Zelano & Branigan, PC

(57) ABSTRACT

The present invention relates to solid pharmaceutical compositions, in particular to oral contraceptives, comprising a progestogen, such as drospirenone; an estrogen, such as ethinylestradiol; a tetrahydrofolic acid or a pharmaceutically acceptable salt thereof, such as calcium 5-methyl-(6S)-tetrahydrofolate; and at least one pharmaceutical acceptable excipient or carrier. The compositions of the invention provide good stability of the tetrahydrofolic acid upon storage while still ensuring a fast and reliable release of the estrogen and the progestogen present in the composition.

11 Claims, 3 Drawing Sheets

(56) References Cited

OTHER PUBLICATIONS

The Merk Index. An encyclopaedia of chemicals, drugs and biologicals. Fourteenth Edition, 2006. p. 585 (Drospirenone).

Chueshov. I. V, et al, "Industrial technology of medicaments," Kharkiv, HFAU MTK-Kniga, 2002, pp. 352-355 (GB translation).

Beringer, P. et al., Remington The Science and Practice and Pharmacy, 21st. ed. Lippincott Williams & Wilkins. 2005.

Gohel, M. C., "A review of co-processed directly compressible excipients.," J. Pharm Pharmaceut Sci., 2005, vol. 8, No. 1, pp. 76-93.

Office Action in related Philippine Patent Application No. 1-2009-500027 dated Apr. 2, 2012.

Wu, J. et al., "Influence of wet granulation and lubrication on the powder and tableting properties of codried product of microcrystalline cellulose with β-cyclodextrin," European Journal of Pharmaceutics and Biopharmaceutics, 2001, vol. 51, pp. 63-69.

Swarbrick, J, Drugs and the Pharmaceutical Sciences. Handbook of Pharmaceutical Granulation, 2005, pp: 175, 204-209, 414, 535-542. 77, 549, 550—18 pages.

Document from *Summons to Oral Proceedings* from the EPO of 18 Apr. 2012, Remington Pharmaceutical Sciences, 18th ed., p. 593 (second column, last paragraph).

Handbook of Pharmaceutical Excipients, Fifth Edition, Edited by Raymond C. Rowe, Paul J. Sheskey and Sian C. Owen, Published by Pharmaceutical Press, 2006, 7 pages.

Keam, S.J., et al., "Ethinylestradiol/Drospirenone: A Review of its Use as an Oral Contraceptive," Treatments in Encocrinology, vol. 2, No. 1, pp. 39-61—Abstract only, Nov. 1, 2003.

Lamers, Y. et al., "Supplementation with [6S]-5-methyltetrahydrofolate or folic acid equally reduces plasma total homocysteine concentrations in healthy women 1-3," The American Journal of Clinical Nutrition, 2004, vol. 79 pp. 473-478.

\* cited by examiner

PHARMACEUTICAL COMPOSITION CONTAINING A TETRAHYDROFOLIC ACID

This application claims the benefit of the filing date of U.S. Provisional Application Ser. No. 60/818,512 filed Jul. 6, 2006, which is incorporated by reference herein.

FIELD OF THE INVENTION

The present invention relates to solid pharmaceutical compositions, in particular to oral contraceptives, comprising a tetrahydrofolic acid, such as calcium 5-methyl-(6S)-tetrahydrofolate. The compositions provided by the present invention allow for good stability of the tetrahydrofolic acid upon storage while still ensuring a fast and reliable release of the estrogen and the progestogen present in the composition.

BACKGROUND OF THE INVENTION

In pregnant women, correction of low folate serum levels takes at least two months, and reserves can last as little as a few weeks. According to a public health service recommendation, all women who can become pregnant should therefore consume 400 µg/day of folic acid to reduce the risk of birth defects (MMWR Morb. Mortal. Wkly. Rep. 1992; 41(RR-14):1-7). Folic acid supplementation immediately before discontinuing oral contraceptive use, or immediately after a positive pregnancy test has been obtained, may be insufficient to optimally protect the developing foetus. In addition, multiple studies of women taking oral contraceptives show decreased folate serum levels relative to negative controls. Postulated mechanisms reported for this phenomenon include decreased absorption of polyglutamates, increased excretion of folic acids, increased production of folate-binding proteins, and induction of folate-dependent hepatic microsomal enzymes. Thus, a decrease of the folate serum level among oral contraceptive users pose an additional risk for such users who become pregnant within three to six months following discontinuation of use.

Accordingly, folic acid should ideally be added to oral contraceptives since adequate folic acid intake during the periconceptional period helps protect against a number of congenital malformations, including neural tube defects, such as spina bifida (an incomplete closure of the spinal cord and spinal column), anencephaly (severe underdevelopment of the brain) and encephalocele (when brain tissue protrudes out to the skin from an abnormal opening in the skull). All of these defects occur during the first 28 days of pregnancy—usually before a woman even knows she is pregnant.

However, incorporation of folic acid in oral contraceptives may pose a serious health risk in that it will suppress symptoms of vitamin B12 deficiency, such as anemia. For example, folic acid can correct the anemia associated with vitamin B12 deficiency, but, unfortunately, folic acid will not correct changes in the nervous system that result from vitamin B12 deficiency. Permanent nerve damage could therefore occur if vitamin B12 deficiency is not treated. The present inventor has therefore suggested to incorporate a tetrahydrofolic acid, such as the natural folic acid derivate, 5-methyl-(6S)-tetrahydrofolic, which is formed in the rather complicated catabolic pathway of the prodrug folic acid, in an oral contraceptive. Incorporation of tetrahydrofolic acids, such as 5-methyl-(6S)-tetrahydrofolic acid, in oral contraceptive could provide all the beneficial effects associated with folic acid, but without the potential disadvantage of masking the anemia of vitamin B12 deficiency.

However, tetrahydrofolic acids are extremely unstable and are highly susceptible to oxidation and moisture. Accordingly, incorporation of a tetrahydrofolic acid into solid oral pharmaceuticals, such as oral contraceptives, represents a big challenge from a formulation point of view. Not only should the resulting solid pharmaceutical composition exhibit a satisfactory stability (with respect to the tetrahydrofolic acid) upon storage, but the very manufacture of the composition itself is considered problematic as exposure to oxidising excipients, humidity and/or open air during the manufacturing process are expected to cause degradation of the tetrahydrofolic acid and should hence be avoided. Furthermore, and as will be apparent from the examples provided herein, the problem of stabilising the tetrahydrofolic acid cannot be solved in isolation as it has turned out that stabilisation of the tetrahydrofolic acid in many cases surprisingly causes insufficient release of other active agents of the composition.

Furthermore, in an oral contraceptive the tetrahydrofolic acid is considered an active ingredient. Therefore, standard stabilisation measures typically used in vitamin supplement products, such as overdosing and broader specification limits, are not applicable in connection with oral contraceptives. Typical overdoses in vitamin supplement products are up to 25% and the dose of Metafolin® in some vitamin supplement products is from 0.6-5.6 mg higher than the recommended daily dose (0.45 mg). Since stability problems are more pronounced when incorporated in pharmaceutical compositions in low concentrations, preparation of stable pharmaceutical compositions containing low dosages of a tetrahydrofolic acid is a challenging task in its own respect.

Nevertheless, the present inventor has surprisingly, via careful selection of critical excipients and/or manufacturing processes, succeeded in preparing oral contraceptives which, one the one hand, exhibit a satisfactory stability with respect to the tetrahydrofolic acid, and, on the other hand, still fulfil the necessary requirements with respect to release, and hence bioavailability, of the estrogen and the progestogen present in the composition.

WO 03/070255 describes kits for contraception and hormone replacement therapy which contain one or more steroids, such as estrogens and progestogens; one or more tetrahydrofolate component; and vitamin B12.

U.S. Pat. No. 6,190,693 is directed to pharmaceutical compositions, suitable as oral contraceptive or in hormone replacement therapy, containing folic acid.

U.S. Pat. No. 6,011,040 relates to the use of tetrahydrofolates for influencing the homocysteine level, in particular for assisting the remethylation of homocysteine.

U.S. Pat. No. 6,441,168 describes stable crystalline salts of 5-methyltetrahydrofolic acid.

SUMMARY OF THE INVENTION

In a first aspect, the present invention relates to a solid pharmaceutical composition comprising a progestogen, an estrogen, a tetrahydrofolic acid or a salt thereof, and at least one pharmaceutical acceptable excipient or carrier.

In another aspect, the present invention relates to a solid oral dosage form comprising a composition according to the invention.

Other aspects of the present invention will be apparent from the below disclosure and the appended claims.

The Y-axis indicates the percentage of calcium 5-methyl-(6S)-tetrahydrofolate remaining after storage, as well as the sum of decomposition products. The X-axis indicates the storage time in months. ● 25° C./60% RH (closed container); ▼ 40° C./75% RH (closed container); ■ 25° C./60% RH (closed container); ▲ 40° C./75% RH (closed container).

Figure 2:
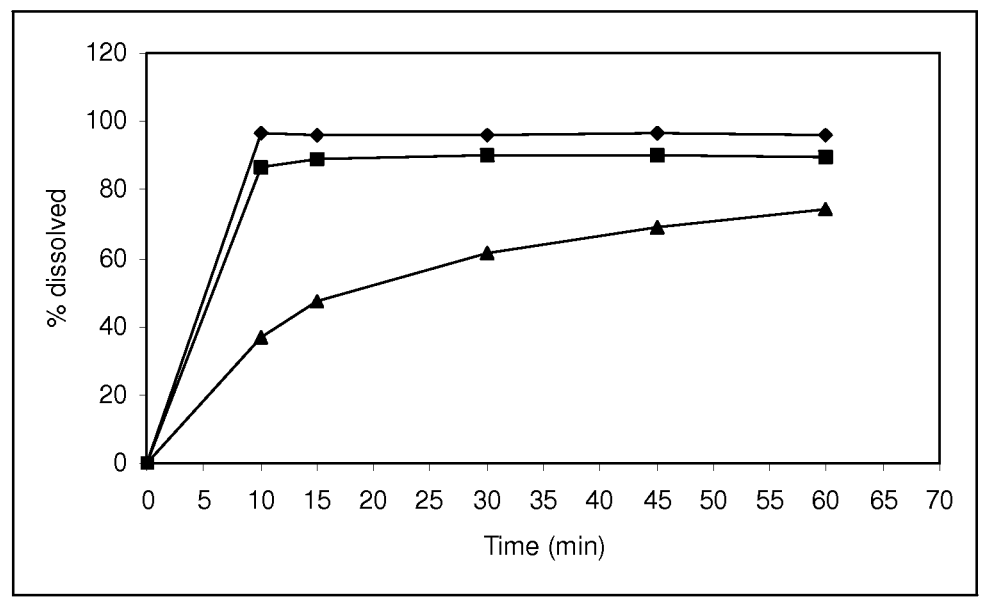

FIG. 2 shows the dissolution of drospirenone, ethinylestradiol and calcium 5-methyl-(6S)-tetrahydrofolate from the tablets prepared in Example 1. The Y-axis indicates the amount dissolved, and the X-axis indicates the dissolution testing time in minutes. ▲ drospirenone; ■ ethinylestradiol; ♦ calcium 5-methyl-(6S)-tetrahydrofolate.

Figure 3:
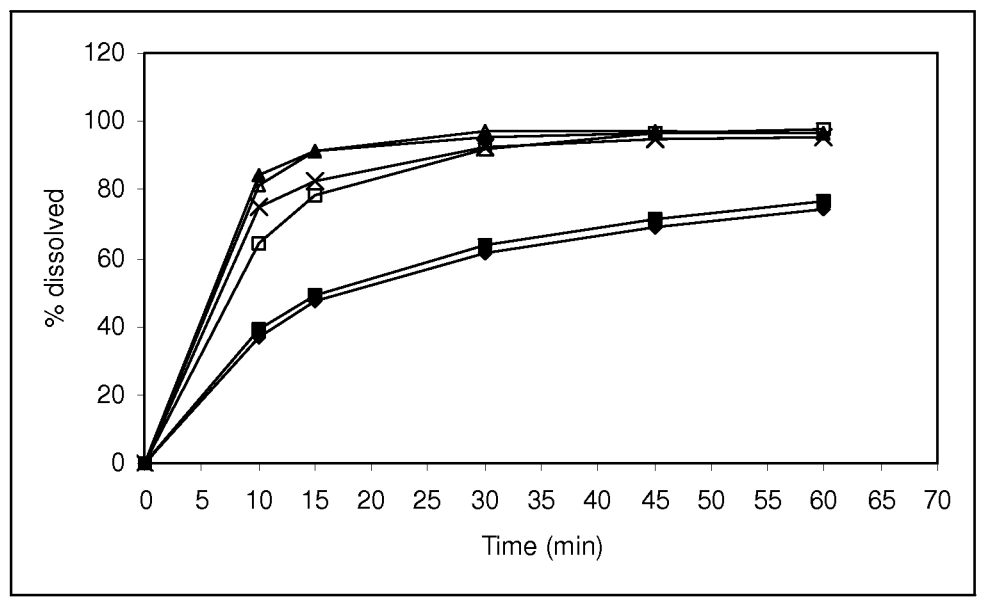

FIG. 3 shows the dissolution of drospirenone from tablets prepared in the Examples. The Y-axis indicates the amount dissolved, and the X-axis indicates the dissolution testing time in minutes. ♦ Example 1; ■ Example 4; ▲ Example 5; × Example 6; Δ Yasmin®; ☐ Yaz®.

DETAILED DESCRIPTION OF THE INVENTION

The term "estrogen" is meant to encompass all compounds (natural or synthetic, steroidal or non-steroidal compounds) exhibiting estrogenic activity. Such compounds encompass inter alia conjugated estrogens, estrogen receptor specific agonists and non-steroidal compounds exhibiting estrogenic activity. The term is further meant to encompass all isomeric and physical forms of the estrogens including hydrates, solvates, salts and complexes, such as complexes with cyclodextrins. More particularly, the estrogen may be selected from the group consisting of ethinylestradiol, estradiol, estradiol sulfamates, estradiol valerate, estradiol benzoate, estrone, mestranol, estriol, estriol succinate and conjugated estrogens, including conjugated equine estrogens such as estrone sulfate, 17β-estradiol sulfate, 17α-estradiol sulfate, equilin sulfate, 17β-dihydroequilin sulfate, 17α-dihydroequilin sulfate, equilenin sulfate, 17β-dihydroequilenin sulfate and 17α-dihydroequilenin sulfate. Particular interesting estrogens are selected from the group consisting of ethinylestradiol, estradiol, estradiol sulfamates, estradiol valerate, estradiol benzoate, estrone, mestranol and estrone sulfate. More preferably, the estrogen is selected from the group consisting of ethinylestradiol, estradiol and mestranol. The most preferred estrogen is ethinylestradiol.

In the present context, the term "progestogen" (also sometimes referred to as "gestagen") covers synthetic hormone compounds which exert anti-estrogenic (counteracting the effects of estrogens in the body) and anti-gonadotropic (inhibiting the production of sex steroids and gonads) properties. Specific examples of progestogens include, but is not limited to, progestogens selected from the group consisting of levonorgestrel, norgestrel, norethindrone (norethisterone), dienogest, norethindrone (norethisterone) acetate, ethynodiol diacetate, dydrogesterone, medroxyprogesterone acetate, norethynodrel, allylestrenol, lynestrenol, quingestanol acetate, medrogestone, norgestrienone, dimethisterone, ethisterone, chlormadinone acetate, megestrol, promegestone, desogestrel, 3-keto-desogestrel, norgestimate, gestodene, tibolone, cyproterone acetate and drospirenone. A particular preferred progestogen is drospirenone.

The term "therapeutically equivalent amount of ethinylestradiol", means that other estrogens are administered in amounts which give rise to the same therapeutic effect as does the specified amount of ethinylestradiol. Likewise, the term "therapeutically equivalent amount of drospirenone" means that other progestogens are administered in amounts which give rise to the same therapeutic effect as does the specified amount of drospirenone. It is routine for those skilled in the art to determine therapeutically equivalent amounts or dosages of such other estrogens and/or progestogens when the effective dose of ethinylestradiol and/or drospirenone is known. For example, the paper of Timmer and Geurts provides guidance of how equivalent doses may be determined (see "Bioequivalence assessment of three different estradiol formulations in postmenopausal women in an open, randomised, single-dose, 3-way cross-over" in European Journal of Drug Metabolism and Pharmacokinetics, 24(1):47-53, 1999). Moreover, reference is made to EP 1 253 607 which provides a detailed description of therapeutically equivalent amounts of ethinylestradiol and estradiol on the one hand, and various progestogens on the other hand. For further details concerning determination of dose equivalents of various estrogens and progestogens, reference is made to "Probleme der Dosisfindung: Sexualhormone" [Problems of Dose-Finding: Sex Hormones]; F. Neumann et al. in "Arzneimittelforschung" (Pharmaceutical Agent Research) 27, 2a, 296-318 (1977), as well as to "Aktuelle Entwicklungen in der hormonalen Kontrazeption" [Current Developments in Hormonal Contraception]; H. Kuhl in Gynäkologe" [Gynecologist] 25: 231-240 (1992).

When used herein, the term "micronised" is intended to mean that the particle size distribution is so that at least 90% of the particles have a particle diameter of less than 30 μm (calculated from the volume distribution curve under the presumption of spherical particles), i.e. a $d_{90}$ value of at the most 30 μm. Therefore, it is important to note that whenever the terms "particle size distribution", "particle diameter", "$d_{90}$", etc. are used herein it should be understood that the specific values or ranges used in connection therewith are always meant to be determined from the volume distribution curve under the presumption of spherical particles.

As will be understood from the present disclosure, including the examples provided herein, it is of utmost importance that the estrogen as well as the progestogen is released in a fast and reliable manner under neutral or acidic conditions. Thus, in the present context, the term "fast-release" or "immediate-release", when used in connection with the term estrogen, means that at least 70% of the estrogen, e.g. ethinylestradiol, is dissolved from the composition within 30 minutes, as determined by the USP XXIX Paddle Method II using water at 37° C. as the dissolution media and 50 rpm as the stirring rate. In a preferred embodiment of the invention at least 75%, more preferably at least 80%, even more preferably at least 85% of the estrogen, e.g. ethinylestradiol, is dissolved from the composition within 30 minutes when assayed as described above.

In an analogous manner, whenever the term "fast-release" or "immediate-release" is used in connection with the term progestogen, this means that at least 70% of the progestogen, e.g. drospirenone, is dissolved from the composition within 30 minutes, as determined by the USP XXIX Paddle Method II using water at 37° C. as the dissolution media and 50 rpm as the stirring rate. In a preferred embodiment of the invention at least 75%, more preferably at least 80%, even more preferably at least 85% of the progestogen, e.g. drospirenone, is dissolved from the composition within 30 minutes when assayed as described above.

Likewise, whenever the term "fast-release" or "immediate-release" is used in connection with the term tetrahydrofolic acid, this means that at least 70% of the tetrahydrofolic acid, e.g. calcium 5-methyl-(6S)-tetrahydrofolate, is dissolved from the composition within 30 minutes, as determined by the USP XXIX Paddle Method II using a 0.03% ascorbic acid aqueous solution (adjusted to pH 3.5 with 0.05 M phosphate buffer) at 37° C. as the dissolution media and 50 rpm as the stirring rate. In a preferred embodiment of the invention at least 75%, more preferably at least 80%, even more preferably at least 85% or at least 90% of the tetrahydrofolic acid, e.g. calcium 5-methyl-(6S)-tetrahydrofolate, is dissolved from the composition within 30 minutes when assayed as described above.

The term "granulate composition" refers to a composition of a powder, wherein the particle size of the powder is either increased upon processing with a liquid or by compression. The liquid may be any kind of suitable aqueous or organic solvents, or mixtures thereof, optionally further comprising a binder. Thus, the term "granulate composition" covers granules, pellets and compressed powder or any particle formed by granulation, pelletation or compression of powder such that a mean particle size ($d_{50}$) of at least about 100 μm is formed.

By the terms "granulating" and "granulation" are understood a mechanical process whereby a powder comprising the active component(s) and excipients are partly agglomerated into particles and/or granules having a larger particle size than the unprocessed powder. In one embodiment, the powdery mixture is contacted with a granulation liquid, which may contain a binder, swelled, partly dissolved or completely dissolved in the granulation liquid. The granulation liquid may be any suitable solvent, but generally aqueous solutions or just water are applicable. In one embodiment, the powdery mixture is contacted with the granulation liquid using suitable equipment for wet-granulation, such as fluidised bed equipment. Furthermore, high shear granulation can be used instead of fluidised bed granulation.

The term "estrogen-cyclodextrin complex" or "estrogen complexed with cyclodextrin" is intended to mean a complex between an estrogen and a cyclodextrin, wherein the estrogen molecule is at least partially inserted into the cavity of a cyclodextrin molecule. The molar ratio between the estrogen and the cyclodextrin may be adjusted to any desirable value. In interesting embodiments of the invention, a molar ratio between the estrogen and the cyclodextrin is from about 2:1 to 1:10, preferably from about 1:1 to 1:5, most preferably from about 1:1 to 1:3, such as 1:1 or 1:2. Furthermore, the estrogen molecule may at least partially be inserted into the cavity of two or more cyclodextrin molecules, e.g. a single estrogen molecule may be inserted into two cyclodextrin molecules to give 2:1 ratio between cyclodextrin and estrogen. Similarly, the complex may contain more than one estrogen molecule at least partially inserted into a single cyclodextrin molecule, e.g. two estrogen molecules may be at least partially inserted into a single cyclodextrin molecule to give a 1:2 ratio between cyclodextrin and estrogen. Complexes between estrogens and cyclodextrins may be obtained by methods known in the art, e.g. as described in U.S. Pat. No. 5,798,338 and EP 1 353 700.

The term "ethinylestradiol-β-cyclodextrin complex" is intended to mean a complex, of any molar ratio, between ethinylestradiol and β-cyclodextrin. However, the ethinylestradiol-β-cyclodextrin complex described herein is typically a complex between one molecule of ethinylestradiol and two molecules of β-cyclodextrin, i.e. a 1:2 ethinylestradiol-β-cyclodextrin complex.

The term "progestogen-cyclodextrin complex" or "progestogen complexed with cyclodextrin" is intended to mean a complex between a progestogen and a cyclodextrin, wherein the progestogen molecule is at least partially inserted into the cavity of a cyclodextrin molecule. The molar ratio between the progestogen and the cyclodextrin may be adjusted to any desirable value. In interesting embodiments of the invention, a molar ratio between the progestogen and the cyclodextrin is from about 2:1 to 1:10, preferably from about 1:1 to 1:5, most preferably from about 1:1 to 1:3. Furthermore, the progestogen molecule may at least partially be inserted into the cavity of two or more cyclodextrin molecules, e.g. a single progestogen molecule may be inserted into two cyclodextrin molecules to give 2:1 ratio between cyclodextrin and progestogen. Similarly, the complex may contain more than one progestogen molecule at least partially inserted into a single cyclodextrin molecule, e.g. two progestogen molecules may be at least partially inserted into a single cyclodextrin molecule to give a 1:2 ratio between cyclodextrin and progestogen. Complexes between progestogens and cyclodextrins may be obtained by methods known in the art, e.g. as described in U.S. Pat. No. 6,610,670 and references therein.

The term "drospirenone-β-cyclodextrin complex" is intended to mean a complex, of any molar ratio, between drospirenone and β-cyclodextrin as described in U.S. Pat. No. 6,610,670. However, the drospirenone-β-cyclodextrin complex is typically a complex between one molecule of drospirenone and three molecules of β-cyclodextrin, i.e. a 1:3 drospirenone-β-cyclodextrin complex.

The term "cyclodextrin" is intended to mean a cyclodextrin or a derivative thereof as well as mixtures of various cyclodextrins, mixtures of various derivatives of cyclodextrins and mixtures of various cyclodextrins and their derivatives. The cyclodextrin may be selected from the group consisting of α-cyclodextrin, β-cyclodextrin, γ-cyclodextrin and derivatives thereof. The cyclodextrin may be modified such that some or all of the primary or secondary hydroxyl groups of the macrocycle are alkylated or acylated. Methods of modifying these hydroxyl groups are well known to the person skilled in the art and many such modified cyclodextrins are commercially available. Thus, some or all of the hydroxyl groups of the cyclodextrin may have been substituted with an O—R group or an O—C(O)—R group, wherein R is an optionally substituted $C_{1-6}$ alkyl, an optionally substituted $C_{2-6}$ alkenyl, an optionally substituted $C_{2-6}$ alkynyl, an optionally substituted aryl or heteroaryl group. Thus, R may be a methyl, an ethyl, a propyl, a butyl, a pentyl, or a hexyl group, i.e. O—C(O)—R may be an acetate. Furthermore, the hydroxyl groups may be per-benzylated, per-benzoylated, benzylated or benzoylated on just one face of the macrocycle, i.e. only 1, 2, 3, 4, 5 or 6 hydroxyl groups is/are benzylated or benzoylated. Naturally, the hydroxyl groups may also be per-alkylated or per-acylated, such as per-methylated or per-acetylated, alkylated or acylated, such as methylated or acetylated, on just one face of the macrocycle, i.e. only 1, 2, 3, 4, 5 or 6 hydroxyl groups is/are alkylated or acylated, such as methylated or acetylated.

As will be understood, the solid composition of the invention contains at least one, such as one, estrogen as defined above. The estrogen may be selected from the group consisting of ethinylestradiol, estradiol, estradiol sulfamates, estradiol valerate, estradiol benzoate, estrone, mestranol and estrone sulphate, including micronised forms thereof. In a highly preferred embodiment of the invention, the estrogen is ethinylestradiol, in particular micronised ethinylestradiol. In one embodiment of the invention, the estrogen, in particular ethinylestradiol, is complexed with a cyclodextrin, such as described in EP 1 353 700. The cyclodextrin is typically selected from the group consisting of α-cyclodextrin, β-cyclodextrin, γ-cyclodextrin and derivatives thereof. In a particular interesting embodiment of the invention, the cyclodextrin is β-cyclodextrin or derivatives thereof. The estrogen-cyclodextrin complex may advantageously be in micronised form.

In addition, the solid composition of the invention contains at least one, such as one, progestogen as defined above. The progestogen may be selected from the group consisting of levo-norgestrel, norgestrel, norethindrone (norethisterone), norethindrone (norethisterone) acetate, dienogest, ethynodiol diacetate, dydrogesterone, medroxyprogesterone acetate, norethynodrel, allylestrenol, lynestrenol, quingestanol acetate, medrogestone, norgestrienone, dimethisterone, ethisterone, chlormadinone acetate, megestrol, promegestone, desogestrel, 3-keto-desogestrel, norgestimate, gestodene, tibolone, cyproterone acetate and drospirenone. In a preferred embodiment of the invention the progestogen is selected from the group consisting of levo-norgestrel, norgestrel, norethindrone (norethisterone), norethindrone (norethisterone) acetate, dienogest, ethynodiol diacetate, desogestrel, norgestimate, gestodene, cyproterone acetate and drospirenone. In a highly preferred embodiment of the invention, the progestogen is drospirenone, in particular micronised drospirenone.

Accordingly, in a preferred embodiment of the invention the composition comprises levo-norgestrel and ethinylestradiol, norgestrel and ethinylestradiol, norethindrone (norethisterone) and ethinylestradiol, norethindrone (norethisterone) acetate and ethinylestradiol, dienogest and ethinylestradiol, ethynodiol diacetate and ethinylestradiol, desogestrel and ethinylestradiol, norgestimate and ethinylestradiol, gestodene and ethinylestradiol, cyproterone acetate and ethinylestradiol, and drospirenone and ethinylestradiol. In a highly preferred embodiment of the invention, the composition comprises drospirenone and ethinylestradiol, more preferably micronised drospirenone and micronised ethinylestradiol, e.g. micronised drospirenone and a micronised ethinylestradiol-cyclodextrin complex, such as micronised drospirenone and a micronised ethinylestradiol-β-cyclodextrin complex.

In addition to the estrogen and the progestogen, the composition of the invention further comprises a tetrahydrofolic acid or a salt thereof. Specific examples of such tetrahydrofolic acids include 5-methyl-(6S)-tetrahydrofolic acid, (6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, including pharmaceutically acceptable salts of these tetrahydrofolic acids and glutamyl derivatives of these tetrahydrofolic acids. In a preferred embodiment of the invention, the tetrahydrofolic acid is 5-methyl-(6S)-tetrahydrofolic acid or a pharmaceutically acceptable salt thereof. In a more preferred embodiment of the invention the salt of 5-methyl-(6S)-tetrahydrofolic acid is an alkaline earth metal salt, in particular the calcium salt. The salt, such as the calcium salt, of 5-methyl-(6S)-tetrahydrofolic acid should preferably be in crystalline form, such as the Type I crystalline form described in U.S. Pat. No. 6,441,168. The type I crystalline form of calcium 5-methyl-(6S)-tetrahydrofolate is commercially available from Merck KGaA under the trademark Metafolin®. It is preferred that the composition of the invention does not contain other vitamins, in particular that the composition of the invention does not contain a vitamin B, such as vitamin B6 and/or vitamin B12. Accordingly, in a preferred embodiment of the invention, the composition contains a tetrahydrofolic acid as the sole vitamin component.

The solid pharmaceutical composition of the invention contains one or more pharmaceutically acceptable excipients. These excipients may, for example, be:

Inert diluents or fillers, such as sucrose, sorbitol, sugars, mannitol, microcrystalline cellulose, starches, sodium chloride, sodium phosphate, calcium carbonate, calcium phosphate, calcium sulfate, lactose, e.g. lactose monohydrate, or a combination thereof. The inert diluent or filler is typically present in an amount from 10-99% by weight of the composition. Preferably, the inert diluent or filler is present in an amount from 50-99% by weight of the composition, more preferably in an amount from 75-99% by weight of the composition, even more preferably in an amount from 80-97% by weight of the composition, most preferably in an amount from 85-97% by weight of the composition. As will be understood from the examples provided herein, highly preferred inert fillers are lactose, in particular lactose monohydrate, and microcrystalline cellulose.

Thus, in a preferred embodiment the composition of the invention comprises lactose monohydrate, microcrystalline cellulose or a combination of lactose monohydrate and microcrystalline cellulose in the amounts indicated supra. Accordingly, in one interesting embodiment of the invention, the composition comprises microcrystalline cellulose. The microcrystalline cellulose is typically present in an amount from 10-99% by weight of the composition, preferably in an amount from 50-99% by weight of the composition, more preferably in an amount from 75-99% by weight of the composition, even more preferably in an amount from 80-97% by weight of the composition, most preferably in an amount from 85-97% by weight of the composition. The microcrystalline cellulose may be the only or sole filler present in the composition, i.e. the composition of the invention may be free from other fillers than microcrystalline cellulose. In another interesting embodiment of the invention, the composition comprises lactose monohydrate. The lactose monohydrate is typically present in an amount from 10-99% by weight of the composition, preferably in an amount from 50-99% by weight of the composition, more preferably in an amount from 75-99% by weight of the composition, even more preferably in an amount from 80-97% by weight of the composition, most preferably in an amount from 85-97% by weight of the composition. The lactose monohydrate may be the only or sole filler present in the composition, i.e. the composition of the invention may be free from other fillers than lactose monohydrate. In a highly preferred embodiment of the invention, the composition comprises microcrystalline cellulose and lactose monohydrate. The microcrystalline cellulose is typically present in an amount from 20-80% by weight of the composition and lactose monohydrate in an amount from 20-80% by weight of the composition. In one embodiment of this aspect of the invention microcrystalline cellulose constitutes the major part of the microcrystalline cellulose-lactose monohydrate filler system, i.e. the composition comprises lactose monohydrate in an amount from 20-60% by weight of the composition and microcrystalline cellulose in an amount from 40-80% by weight of the composition, such as lactose monohydrate in an amount from 20-45% by weight of the composition and microcrystalline cellulose in an amount from 40-70% by weight of the composition, e.g. lactose monohydrate in an amount from 25-36% by weight of the composition and microcrystalline cellulose in an amount from 52-63% by weight of the composition. The microcrystalline cellulose and the lactose monohydrate may be the only fillers present in the composition, i.e. the composition of the invention may be free from other fillers than microcrystalline cellulose and lactose monohydrate. In another, and currently preferred, embodiment of this aspect of the invention lactose monohydrate constitutes the major part of the microcrystalline cellulose-lactose monohydrate filler system, i.e. the composition comprises microcrystalline cellulose in an amount from 20-60% by weight of the composition and lactose monohydrate in an amount from 40-80% by weight of the composition. More preferably, the composition comprises microcrystalline cellulose in an amount from 20-45% by weight of the composition and lactose monohydrate in an amount from 40-70% by weight of the composition. Most preferably, the composition comprises microcrystalline cellulose in an amount from 25-36% by weight of the composition and lactose monohydrate in an amount from 52-63% by weight of the composition. The microcrystalline cellulose and the lactose monohydrate may be the only fillers present in the composition, i.e. the composition of the invention may be free from other fillers than microcrystalline cellulose and lactose monohydrate.

Microcrystalline cellulose is commercially available in different particle sizes and moisture grades. Examples of commercially available microcrystalline cellulose preparations include the Avicel® PH-series from FMC Biopolymer, the Emcocel® M-series from Penwest Pharmaceuticals Co. and the Vivapur®-series from Rettenmaier & Söhne GmbH. A particular preferred commercial product to be used for the purposes described herein is Avicel® PH-101. Likewise, various lactose monohydrate grades having different physical properties, such as particle size distribution and flow characteristics, are commercially available. The grade of the lactose monohydrate may vary dependent on the specific dosage form to be prepared. For example, direct-compression grades of lactose monohydrate, such as Tablettose® (agglomerated) or grades for powder blends, such as Pharmatose® DCL 11 (spray-dried), have better flow properties and are more compressible than powdered or crystalline lactose monohydrate. Such lactose monohydrate preparations are not particularly preferred for the purposes described herein. Rather, the more fine grade lactose monohydrate preparations are preferred, such as powdered or crystalline lactose monohydrate, in particular crystalline lactose monohydrate where 90% of the particles have a diameter of less than 0.1 mm.

Binders,
such as sucrose, glucose, sorbitol, acacia, alginic acid, sodium alginate, gelatine, starch, pregelatinised starch, magnesium aluminium silicate, carboxymethylcellulose sodium (CMC sodium), methylcellulose, ethylcellulose, hydroxypropylmethylcellulose (HPMC), hydroxy-propylcellulose (HPC), polyvinylacetate or polyethylene glycol. The binder is typically present in an amount from 0.1-10% by weight of the composition. Preferably, the binder is present in an amount from 0.2-5% by weight of the composition, such as from 0.5-5% by weight of the composition, more preferably in an amount from 1-3% by weight of the composition. In a preferred embodiment of the invention, the binder is HPC. It should be noted that while polyvinylpyrrolidone (PVP) in many situations is the "binder of choice", in particular in connection with wet granulation processes, incorporation of PVP in the composition of the invention is not desirable due to the oxidising potential of this excipient. In fact, it was found by the present inventor that PVP accelerated the breakdown of 5-methyl-(6S)-tetrahydrofolic acid (data not shown).

Thus, due to degradation of the oxidation-sensitive tetrahydrofolic acid, the amount of PVP in the composition of the invention should be kept at an absolute minimum and should preferably be avoided. Thus, the composition of the invention typically contains less than 2% PVP by weight of the composition, preferably less than 1% PVP by weight of the composition, more preferably less than 0.5% PVP by weight of the composition. Most preferably, the composition of the invention is essentially free from PVP.

Lubricants, including glidants and antiadhesives,
such as magnesium stearate, zinc stearate, stearic acid, silicas, hydrogenated vegetable oils or talc. The lubricant is typically present in an amount from 0.1-10% by weight of the composition. Preferably, the lubricant is present in an amount from 0.2-5% by weight of the composition, such as from 0.5-5% by weight of the composition, more preferably in an amount from 1-3% by weight of the composition. In a preferred embodiment of the invention, the lubricant is magnesium stearate.

Disintegrants,
such as, sodium starch glycolate, maize starch, rice starch, potato starch, cross-linked povidone or carboxymethylcellulose-based disintegrants. Carboxymethylcellulose-based disintegrants may be present as free acid, but is preferably in the form of a salt, e.g. in the form of an alkali metal salt, such as the potassium salt or the sodium salt, in particular the sodium salt, or in the form of a salt of a divalent metal ion, such as the magnesium salt, the calcium salt or the zinc salt, in particular the calcium salt. The carboxymethylcellulose-based disintegrant may be cross-linked or non-cross-linked. Specific examples of preferred non-cross-linked carboxymethylcellulose-based disintegrants include carboxymethyl-cellulose calcium (carmellose calcium) and carboxymethylcellulose sodium (carmellose sodium), in particular carboxymethylcellulose calcium. In a highly preferred embodiment of the invention the carboxymethylcellulose-based disintegrant is cross-linked. A specific example of a preferred cross-linked carboxymethylcellulose-based disintegrant is cross-linked carboxymethylcellulose sodium (croscarmellose sodium). Croscarmellose sodium is commercially available under the tradenames Ac-Di-Sol®, Explocel® and Solutab®. The disintegrant is typically present in an amount from 0.1-10% by weight of the composition. Preferably, the disintegrant is present in an amount from 0.2-5% by weight of the composition, such as from 0.5-5% by weight of the composition, more preferably in an amount from 1-4% by weight of the composition.

Surfactants and wetting agents,
such as naturally occurring phosphatides, e.g. lechitin or soybean lechitin; condensation products of ethylene oxide with e.g. a fatty acid, a long chain fatty alcohol, or a partial ester derived from fatty acids and a hexitol or a hexitol anhydride, for example polyoxyethylene stearate, polyoxyethylene sorbitol monooleate, polyoxyethylene sorbitan monooleate, etc.; or salts of long-chain aliphatic phosphates, such as sodium lauryl sulphate.

Examples of other pharmaceutically acceptable excipients which may be incorporated in the solid pharmaceutical composition of the invention include colorants, flavouring agents, plasticizers, humectants, buffering agents, etc.

In those cases where the pharmaceutical formulation is in the form of a solid oral dosage form, in particular a solid unit dosage form (e.g. a tablet, sachet or capsule, in particular a tablet), the dosage form is adapted for oral administration and may be provided with a coating, such as a film coating, a sugar coating, or the like. Thus, a suitable coating for the dosage form according to the invention may, for example, be a sugar coating or a film coating based on one or more of the ingredients: Hydroxypropylmethylcellulose (HPMC), methylcellulose, ethylcellulose, hydroxyethylmethylcellulose, hydroxypropylcellulose, carboxymethylcellulose sodium, acrylate polymers (e.g. Eudragit®), polyethylene glycols or polyvinylpyrrolidone.

In a highly preferred embodiment of the invention, the dosage form is in the form of a tablet, preferably a coated tablet, more preferably a film-coated tablet.

The uncoated tablet typically has a weight in the range from 50-150 mg, such as in the range of 60-125 mg, e.g. in the range of 60-100 mg, preferably in the range of 70-90 mg, e.g. about 80 mg.

The dosage form typically contains an amount of progestogen corresponding to a therapeutically equivalent amount of drospirenone from 0.25-4 mg, such as in an amount corresponding to a therapeutically equivalent amount of drospirenone from 1-4 mg, e.g. in an amount corresponding to a therapeutically equivalent amount of drospirenone from 2-4 mg, preferably in an amount corresponding to a therapeutically equivalent amount of drospirenone from 2.5-3.5 mg, most preferably in an amount corresponding to a therapeutically equivalent amount of drospirenone of about 3 mg. As discussed above, the progestogen may be complexed with a cyclodextrin.

Moreover, the solid oral dosage form typically contains an amount of estrogen corresponding to a therapeutically equivalent amount of ethinylestradiol from 0.005-0.05 mg, such as in an amount corresponding to a therapeutically equivalent amount of ethinylestradiol from 0.01-0.05 mg, preferably in an amount corresponding to a therapeutically equivalent amount of ethinylestradiol from 0.015-0.035 mg, most preferably in an amount corresponding to a therapeutically equivalent amount of ethinylestradiol of about 0.02 mg or about 0.03 mg. As discussed above, the estrogen may be complexed with a cyclodextrin.

Thus, in a particular interesting embodiment of the invention, the dosage form comprises 0.25-4 mg drospirenone and 0.005-0.05 mg ethinylestradiol, such as 1-4 mg drospirenone and 0.005-0.05 mg ethinylestradiol, e.g. 2-4 mg drospirenone and 0.01-0.05 mg ethinylestradiol, preferably 2.5-3.5 mg drospirenone and 0.015-0.035 mg ethinylestradiol, more preferably about 3 mg drospirenone and about 0.03 mg ethinylestradiol, or about 3 mg drospirenone and about 0.02 mg ethinylestradiol.

While the preferred progestogen is drospirenone, incorporation of other progestogens is indeed also within the scope of the present invention. More particularly, the dosage form may comprise desogestrel in an amount from 0.05-0.5 mg, preferably from 0.075-0.25 mg, such as 0.1 mg, 0.125 mg or 0.15 mg; ethynodiol diacetate in an amount from 0.25-2 mg, preferably 0.75-1.5 mg, such as 1 mg; levo-norgestrel in an amount from 0.025-0.3 mg, preferably from 0.075-0.25 mg, such as 0.1 mg or 0.15 mg; norethindrone (norethisterone) in an amount from 0.2-1.5 mg, preferably 0.3-1.25 mg, such as 0.4 mg, 0.5 mg or 1 mg; norethindrone (norethisterone) acetate in an amount from 0.5-2 mg, preferably 1-1.5 mg, such as 1 mg or 1.5 mg; norgestrel in an amount from 0.1-1 mg, preferably from 0.25-0.75 mg, such as 0.3 mg or 0.5 mg; norgestimate in an amount from 0.1-0.5 mg, preferably 0.15-0.3 mg, such as 0.18 mg, 0.215 mg or 0.25 mg; cyproterone acetate in an amount from 1-2 mg, preferably 2 mg; dienogest in an amount from 2-3 mg, preferably 2 mg; gestodene in an amount from 0.05-0.1 mg, preferably from 0.06-0.075 mg, such as 0.075 mg; and tibolone in an amount from 2-3 mg, such as 2.5 mg. Likewise, while the preferred estrogen is ethinylestradiol, incorporation of other estrogens is indeed also within the scope of the present invention. More particularly, the dosage form may comprise estradiol in an amount from 1-4 mg or mestranol from 0.01-0.1 mg, preferably from 0.025-0.075 mg, such as 0.05 mg. Specific examples of progestogen-estrogen combinations, including preferred dosages, are given in the below table:

| Progestogen | Estrogen | Product name |
| --- | --- | --- |
| Drospirenone | Ethinylestradiol | |
| 0.25-4 mg | 0.005-0.05 mg | |
| 1-4 mg | 0.005-0.05 mg | |
| 2-4 mg | 0.01-0.05 mg | |
| 2.5-3.5 mg | 0.015-0.035 mg | |
| 3 mg | 0.03 mg | Yasmin ®, monophasic |
| 3 mg | 0.02 mg | Yaz ®, monophasic, 24 day regimen |
| cyproterone acetate | Ethinylestradiol | |
| 1-2 mg | 0.01-0.05 mg | |
| 2 mg | 0.035 mg | Diane-35 ®, monophasic |
| Dienogest | Ethinylestradiol | |
| 2-3 mg | 0.01-0.05 mg | |
| 2 mg | 0.03 mg | Valette ®, monophasic |
| Gestodene | Ethinylestradiol | |
| 0.05-0.1 mg | 0.01-0.05 mg | |
| 0.06-0.075 mg | 0.015-0.035 mg | |
| 0.075 mg | 0.03 mg | Femovan ®, monophasic |
| Desogestrel | Ethinylestradiol | |
| 0.05-0.5 mg | 0.01-0.05 mg | |
| 0.075-0.25 mg | 0.015-0.035 mg | |
| 0.15 mg | 0.03 mg | Desogen ®, monophasic |
| 0.15 mg (21 days) | 0.02 mg (21 days) 0.01 mg (5 days) | Mircette ®, biphasic |
| 0.1 mg | 0.025 mg | Cyclessa ®, triphasic |
| 0.125 mg | 0.025 mg | |
| 0.15 mg | 0.025 mg | |
| Ethynodiol diacetate | Ethinylestradiol | |
| 0.25-2 mg | 0.01-0.05 mg | |
| 0.75-1.5 mg | 0.015-0.035 mg | |

| | | -continued |
|---|---|---|
| 1 mg | 0.035 mg | Demulen 1/35 ®, monophasic |
| 1 mg | 0.05 mg | Demulen 1/50 ®, monophasic |

| Levo-norgestrel | Ethinylestradiol | |
|---|---|---|
| 0.025-0.3 mg | 0.01-0.05 mg | |
| 0.075-0.25 mg | 0.015-0.035 mg | |
| 0.1 mg | 0.02 mg | Levlite ®, Miranova ®, monophasic |
| 0.125 mg | 0.03 mg | Monostep ®, monophasic |
| 0.15 mg | 0.03 mg | Levlen ®, Microgynon ®, monophasic |
| 0.05 mg | 0.03 mg | Triphasil ®, Novastep ®, Triquilar ®, |
| 0.075 mg | 0.04 mg | triphasic |
| 0.125 mg | 0.03 mg | |

| Norethindrone | Ethinylestradiol | |
|---|---|---|
| 0.2-1.5 mg | 0.01-0.05 mg | |
| 0.3-1.25 mg | 0.015-0.035 mg | |
| 0.4 mg | 0.035 mg | Ovcon-35 ®, monophasic |
| 0.5 mg | 0.035 mg | Modicon ®, monophasic |
| 1 mg | 0.035 mg | Ortho-Novum 1-35 ®, monophasic |
| 1 mg | 0.05 mg | Ovcon 50 ®, monophasic |
| 0.5 mg | 0.035 mg | Ortho Novum 10-11 ®, biphasic |
| 1 mg | 0.035 mg | |
| 0.5 mg | 0.035 mg | Ortho Novum 7-7-7 ®, triphasic |
| 0.75 mg | 0.035 mg | |
| 1 mg | 0.035 mg | |
| 0.5 mg | 0.035 mg | Tri-Norinyl ®, triphasic |
| 1 mg | 0.035 mg | |
| 0.5 mg | 0.035 mg | |

| Norethindrone | Mestranol | |
|---|---|---|
| 0.2-1.5 mg | 0.01-0.1 mg | |
| 0.3-1.25 mg | 0.025-0.075 mg | |
| 1 mg | 0.050 mg | Ortho-Novum 1-50 ®, monophasic |

| Norethindrone acetate | Ethinylestradiol | |
|---|---|---|
| 0.5-2 mg | 0.01-0.05 mg | |
| 1-1.5 mg | 0.015-0.035 mg | |
| 1 mg | 0.02 mg | Loestrin 1-20 ®, monophasic |
| 1 mg | 0.02 mg | Loestrin 24 FE ®, 24 day regimen |
| 1.5 mg | 0.03 mg | Loestrin 1.5-30 ®, monophasic |
| 1 mg | 0.02 mg | Estrostep ®, triphasic |
| 1 mg | 0.03 mg | |
| 1 mg | 0.035 mg | |

| Norgestrel | Ethinylestradiol | |
|---|---|---|
| 0.1-1 mg | 0.01-0.05 mg | |
| 0.25-0.75 mg | 0.015-0.035 mg | |
| 0.3 mg | 0.03 mg | Lo-Ovral ®, monophasic |
| 0.5 mg | 0.05 mg | Ovral ®, monophasic |

| Norgestimate | Ethinylestradiol | |
|---|---|---|
| 0.1-0.5 mg | 0.01-0.05 mg | |
| 0.15-0.3 mg | 0.015-0.035 mg | |
| 0.25 mg | 0.025 mg | Ortho Tri-Cyclen Lo ® |
| 0.25 mg | 0.035 mg | Ortho-Cyclen ®, monophasic |
| 0.18 mg | 0.035 mg | Ortho- Tri-Cyclen ®, triphasic |
| 0.215 mg | 0.035 mg | |
| 0.25 mg | 0.035 mg | |
| 0.18 mg | 0.025 mg | Ortho- Tri-Cyclen Lo ®, triphasic |
| 0.215 mg | 0.025 mg | |
| 0.25 mg | 0.025 mg | |

The solid oral dosage form typically contains a tetrahydrofolic acid in an amount from 0.1-5 mg, such as in an amount from 0.1-2.5 mg, e.g. in an amount from 0.2-0.8 mg, preferably in an amount from 0.3-0.7 mg, more preferably in an amount from 0.4-0.6 mg, most preferably in an amount from 0.42-0.49 mg. As explained above, the tetrahydrofolic acid is preferably 5-methyl-(6S)-tetrahydrofolic acid or a pharmaceutically acceptable salt thereof, such as an alkaline earth metal salt, in particular the calcium salt. The salt, such as the calcium salt, of 5-methyl-(6S)-tetrahydrofolic acid should preferably be in crystalline form, such as the Type I crystalline form described in U.S. Pat. No. 6,441,168.

The various excipients may be incorporated in the dosage form of the invention in the amount indicated previously. However, in an interesting embodiment of the invention the dosage form comprises microcrystalline cellulose, lactose monohydrate or a combination of microcrystalline cellulose and lactose monohydrate. Accordingly, in one interesting embodiment of the invention the dosage form comprises microcrystalline cellulose in an amount from 5-80 mg, such as from 10-80 mg. Preferably, the dosage form comprises microcrystalline cellulose in an amount from 40-80 mg. More preferably, the dosage form comprises microcrystalline cellulose in an amount from 60-80 mg. Even more preferably, the dosage form comprises microcrystalline cellulose in an amount from 65-80 mg. Most preferably, the dosage form comprises microcrystalline cellulose in an amount from 65-77 mg. The microcrystalline cellulose may be the only or sole filler present in the dosage form, i.e. the dosage form of the invention may be free from other fillers than microcrystalline cellulose. In another interesting embodiment of the invention the dosage form comprises lactose monohydrate in an amount from 5-80 mg, such as from 10-80 mg. Preferably, the dosage form comprises lactose monohydrate in an amount from 40-80 mg. More preferably, the dosage form comprises lactose monohydrate in an amount from 60-80 mg. Even more preferably, the dosage form comprises lactose monohydrate in an amount from 65-80 mg. Most preferably, the dosage form comprises lactose monohydrate in an amount from 65-77 mg. The lactose monohydrate may be the only or sole filler present in the dosage form, i.e. the dosage form of the invention may be free from other fillers than lactose monohydrate. In a highly interesting embodiment of the invention the dosage form comprises microcrystalline cellulose in an amount from 15-65 mg and lactose monohydrate in an amount from 15-65 mg. In one embodiment of this aspect of the invention microcrystalline cellulose constitutes the major part of the microcrystalline cellulose-lactose monohydrate filler system, i.e. the dosage form comprises lactose monohydrate in an amount from 15-50 mg and microcrystalline cellulose in an amount from 25-65 mg. Even more preferably, the dosage form comprises lactose monohydrate in an amount from 15-35 mg and microcrystalline cellulose in an amount from 30-55 mg. Most preferably, the dosage form comprises lactose monohydrate in an amount from 20-30 mg and microcrystalline cellulose in an amount from 40-50 mg. In another, and currently preferred, embodiment of this aspect of the invention lactose monohydrate constitutes the major part of the microcrystalline cellulose-lactose monohydrate filler system, i.e. the dosage form comprises microcrystalline cellulose in an amount from 15-50 mg and lactose monohydrate in an amount from 25-65 mg. Even more preferably, the dosage form comprises microcrystalline cellulose in an amount from 15-35 mg and lactose monohydrate in an amount from 30-55 mg. Most preferably, the dosage form comprises microcrystalline cellulose in an amount from 20-30 mg and lactose monohydrate in an amount from 40-50 mg.

The present inventor surprisingly found that the problem concerning stability of a tetrahydrofolic acid as well as the problem associated with obtaining fast-release of the progestogen from tablets prepared by direct compression could in fact be, at least partly, solved by preparing the composition by means of granulation, i.e. in a preferred embodiment the composition of the invention is a granulate composition; Due to the exposure to mechanical stress and humidity during the granulation process, the skilled person would not contemplate preparing a tetrahydrofolic acid-containing composition by granulation as he would expect the air- and moisture-sensitive tetrahydrofolic acid to degrade significantly under such manufacturing conditions. Nevertheless, the present inventor went against this prejudice and found, by combining granulation with proper selection of excipients, that a stable (with respect to the tetrahydrofolic acid) granulate composition, which simultaneously fulfilled the necessary requirements with respect to fast-release of the estrogen and the progestogen, could be obtained.

Thus, as will be understood from the discussion supra as well as the examples provided herein, the composition of the invention is preferably prepared by means of a granulation process, i.e. the drug substances, including the tetrahydrofolic acid, together with appropriate excipients, are subjected to a granulation process, preferably a wet granulation process, such as a fluid bed granulation process. Accordingly, in a preferred embodiment the composition of the invention is a granulate composition. After the granulation process, the granules can be processed further into the final dosage form. In one embodiment of the invention the granules may be filled into sachets or capsules, such as hard gelatine capsules. However, in a preferred embodiment of the invention the granules are processed into tablets by compression and subsequently film-coated. As will be understood, the tetrahydrofolic acid may, in one embodiment of the invention, be added before or during the granulation process. In this case the tetrahydrofolic acid can be regarded as an "inner phase" component since it forms part of the granule as such. In another embodiment of the invention, the tetrahydrofolic acid is added to the granules at the end of the granulations process, or after the granulation process has been completed, i.e. the tetrahydrofolic acid can be regarded as an "outer component". Thus, the tetrahydrofolic acid may be incorporated in the granules as an "inner phase" component, as an "outer phase" component or as a combination thereof. In a preferred embodiment of the invention, the tetrahydrofolic acid is present as an "outer phase" component.

Accordingly, the present invention is also directed to a process for the manufacture of a composition according to the invention, which comprises the steps of:
(i) subjecting a progestogen, an estrogen and at least one pharmaceutical acceptable excipient to a granulation process,
(ii) mixing a tetrahydrofolic acid or a salt thereof with the granules formed in step (i), and
(iii) optionally continuing the granulation process, and/or
(iv) optionally collecting the granules.

In step (i), the progestogen, the estrogen and at least one pharmaceutical acceptable excipient, such as lactose monohydrate, microcrystalline cellulose or a combination thereof, is loaded into a granulator, preferably a fluidised bed granulator. A granulation liquid, typically containing a binder such as HPC, is then applied and, in the case of fluidised bed granulation, the granulation liquid is sprayed continuously onto the fluidised bed while heating the air stream of the fluidised bed. In order to avoid degradation of the tetrahydrofolic acid during the granulation process, it is preferred that the tetrahydrofolic acid or a salt thereof is mixed with the granules formed in step (i) at the end of, near the end of, or after, the granulation process. If desired, the granulation process may, however, be continued after addition of the tetrahydrofolic acid. Typically, a disintegrant and a lubricant are also mixed with the granules formed in step (i) together with the tetrahydrofolic acid.

The granules obtainable by the above process may be further process into a desired dosage form, e.g. a tablet, by compression. Thus, in a further aspect the present invention is also directed to a process for the manufacture of a solid oral dosage form according to the invention, which comprises the steps of:
(i) preparing granules according to the process according to the invention, and
(ii) formulating the granules into solid oral dosage forms.

While the composition of the invention is preferably in the form of a granulate composition which may subsequently be processed into the desired dosage form, it is contemplated that in case low-dose progestogen dosage forms are prepared, the fast-release problems associated with this active component will not be as pronounced as when higher doses of the progestogen, in particular drospirenone, are required in the dosage form. Accordingly, the present invention also relates to a tablet, in particular a tablet prepared by direct compression, comprising a progestogen, an estrogen, a tetrahydrofolic acid or a pharmaceutically acceptable salt thereof, and at least one pharmaceutical acceptable excipient or carrier, wherein the amount of the progestogen is from 0.025-1.5 mg, such as 0.025-1 mg, 0.05-1 mg, 0.075-0.75 mg or 0.1-0.5 mg. It should be understood that all statements made above, in particular the statements concerning preferred excipients, preferred progestogens, preferred estrogens, preferred tetrahydrofolic acids as well as relevant amounts of such components, apply mutatis mutandis to this aspect of the invention.

Furthermore, while the composition of the invention preferably comprises a progestogen as well as an estrogen, it should be understood that compositions and dosage forms may be prepared according to the present invention, but where such compositions and dosage forms does not contain an estrogen. One example of such a dosage form is Microlut® (also known as the "mini-pill"), which contains 0.03 mg levo-norgestrel and no estrogen. Accordingly, in a further aspect, the present invention relates to a solid pharmaceutical composition comprising a progestogen, a tetrahydrofolic acid or a pharmaceutically acceptable salt thereof, and at least one pharmaceutical acceptable excipient or carrier. As will be understood, all statements made above, in particular the statements concerning preferred excipients, preferred progestogens, preferred tetrahydrofolic acids as well as relevant amounts of such components, apply mutatis mutandis to this aspect of the invention.

Concerning the stability of the tetrahydrofolic acid, the normal specification limits of an active ingredient must be applied. A suitable reference is the USP XXIX monograph "Folic acid tablets", which specifies that a content of 90-115% of the declared amount of the folic acid must subsequently be identifiable in the product. The compositions and the dosage forms provided by the present invention fulfil the above-mentioned regulatory requirements. Expressed differently, the composition or the dosage form of the invention has a stability such that at least 80% of the initial amount of the tetrahydrofolic acid is present in the composition or in the dosage form after storage in a closed container for 24 months at 25° C. and 60% relative humidity. In addition, or in the alternative, the composition or the dosage form of the invention has a stability such that at least 90% of the initial amount of the tetrahydrofolic acid is present in the composition or in the dosage form after storage in a closed container for 12 months at 25° C. and 60% relative humidity. In the present context, the term "initial content", when used in connection with a tetrahydrofolic acid, refers to the measured amount of the tetrahydrofolic acid determined immediately after the manufacture of the composition or dosage form or, alternatively, after storage in a closed container for not more than 5 days at 25° C. and 60% relative humidity. Thus, the term "initial amount" neither refers to the declared amount of the tetrahydrofolic acid, nor to the theoretical amount of (added) tetrahydrofolic acid, but rather to the measured amount of the tetrahydrofolic acid present in the composition or dosage form determined immediately after its manufacture or after storage for a short period of time as described above.

In another embodiment, the composition or the dosage form of the invention has a stability such that at least 80% of the declared amount of the tetrahydrofolic acid is present in the composition or in the dosage form after storage in a closed container for 24 months at 25° C. and 60% relative humidity. In addition, or in the alternative, the composition or the dosage form of the invention has a stability such that at least 90% of the declared amount of the tetrahydrofolic acid is present in the composition or in the dosage form after storage in a closed container for 12 months at 25° C. and 60% relative humidity. In the present context, the term "declared amount" refers to the officially declared amount of the tetrahydrofolic acid present in the composition or the dosage. The declared amount of the tetrahydrofolic acid is normally apparent from the information provided in the leaflet.

In still another embodiment, the composition or the dosage form of the invention has a stability such that the sum of the tetrahydrofolic acid decomposition products is at the most 10%, preferably at the most 8%, more preferably at the most 6%, even more preferably at the most 5%, most preferably at the most 4%, after storage in a closed container for 6 months or 12 months at 25° C. and 60% relative humidity. The sum of tetrahydrofolic acid decomposition products may be determined as described in the section entitled "Determination of decomposition products" herein.

In yet another embodiment, the composition or the dosage form of the invention has a stability such that the sum of tetrahydrofolic acid decomposition products is at the most 10%, preferably at the most 8%, more preferably at the most 6%, even more preferably at the most 5%, most preferably at the most 4%, after storage in a closed container for 1 month, 2 months or 3 months at 40° C. and 75% relative humidity. The sum of the tetrahydrofolic acid decomposition products may be determined as described in the section entitled "Determination of decomposition products" herein.

As is evident from the disclosure herein, the compositions or the dosage forms of the invention are suitable for inhibition of ovulation in a female, i.e. for providing female contraception. In addition, due to the presence of a tetrahydrofolic acid or a salt thereof, the compositions and dosage forms of the invention are also useful for the treatment or prevention of folate deficiency, including anemia and bleedings.

In a further particular embodiment, the present invention relates to a pharmaceutical preparation or kit consisting essentially of 21, 22, 23 or 24, in particular 21 or 24, separately packed and individually removable solid oral dosage units according to the invention placed in a packaging unit, and 7, 6, 5 or 4, in particular 7 or 4, separately packed and individually removable solid oral dosage units containing a tetrahydrofolic acid as the sole active agent placed in a packaging unit.

The dosage forms containing a tetrahydrofolic acid as the sole active agent may be prepared by any method known in the art as long as the tetrahydrofolic acid still fulfils the stability criteria discussed herein. In one embodiment, the dosage form containing a tetrahydrofolic acid as the sole active agent is essentially identical to the dosage forms described herein, but no progestogens and estrogens are included.

The preparation (or kit) may be a one-phase preparation, i.e. a preparation wherein the amounts of the progestogen and the estrogen remain constant for the entire 21-, 22-, 23- or 24-day period. Alternatively, amounts of either or both active agents (i.e. the progestogen and the estrogen) may be varied over the 21-, 22-, 23- or 24-day period to generate a multiple-phase preparation, e.g. a two- or three-phase preparation, such as described in, e.g., U.S. Pat. No. 4,621,079. Thus, while the preparation may be a one-phase or a multiple phase preparation, the amount of the tetrahydrofolic acid preferably remains constant throughout the entire cycle, i.e. for all 28 days.

A packaging unit comprising the dosage forms described above may be prepared in a manner analogous to that of making other oral contraceptives. This may for instance be a conventional blister pack or any other form known for this purpose, for instance a pack comprising the appropriate number of dosage units (in this case typically 28 or a multiple of 28) in a sealed blister pack with a cardboard, paperboard, foil or plastic backing and enclosed in a suitable cover.

Likewise, the compositions or the dosage forms of the invention are also suitable for treatment of diseases, conditions or symptoms associated with deficient endogenous levels of estrogen in women. In this case, the above-mentioned progestogens are preferably combined with an estrogen selected from the group consisting of estradiol, estradiol sulfamates, estradiol valerate, estradiol benzoate. A specific example of a preferred dosage form comprises 0.25-3 mg drospirenone and 0.5-2 mg estradiol, such as 1-3 mg drospirenone and 0.5-2 mg estradiol, preferably 1.5-2.5 mg drospirenone and 0.5-1.5 mg estradiol, more preferably about 2 mg drospirenone and about 1 mg estradiol (Angeliq®). Other examples include compositions or dosage forms comprising estradiol valerate and cyproterone acetate, estradiol valerate and dienogest, ethinylestradiol and gestodene, and ethinylestradiol and levo-norgestrel. Deficient levels of estrogen can occur for a variety of reasons. For example, deficient levels of estrogen may be caused by e.g. natural menopause, peri-menopause, post-menopause, hypogonadism, castration or primary ovarian failure. Low levels of estrogen, irrespective of the cause, lead to an overall decreased quality of life for women. Symptoms, diseases and conditions range from merely being inconvenient to life threatening. The compositions and dosage forms described herein provide effective alleviation of all physiological and psychological signs of estrogen deficiency. Transient symptoms, such as vasomotor signs and psychological symptoms are certainly embodied with the realm of therapy. Vasomotor signs comprise but are not limited to hot flushes, sweating attacks such as night sweats, and palpitations. Psychological symptoms of estrogen deficiency comprise, but are not limited to, insomnia and other sleep conditions, poor memory, loss of confidence, mood changes, anxiety, loss of libido, difficulties in concentration, difficulty in making decisions, diminished energy and drive, irritability and crying spells. The treatment of the aforementioned symptoms can be associated with the peri-menopausal phase of a woman's life or after, sometimes long time after, menopause. It is anticipated that the compositions and dosage forms described herein are applicable to these and other transient symptoms during the peri-menopausal phase, menopause, or post-menopausal phase. Moreover, the aforementioned symptoms can be alleviated if the cause of the estrogen deficiency is hypogonadism, castration or primary ovarian failure. In another embodiment of the invention, the compositions or dosage forms described herein are used for the treatment of permanent effects of estrogen deficiency. Permanent effects comprise physical changes such as urogenital atrophy, atrophy of the breasts, cardiovascular disease, changes in hair distribution, thickness of hair, changes in skin condition and osteoporosis. Urogenital atrophy, and conditions associated with it such as vaginal dryness, increase in vaginal pH and subsequent changes in flora, or events which lead to such atrophy, such as decreases in vascularity, fragmentation of elastic fibres, fusion of collagen fibres, or decreases in cell volume, are symptoms thought to be particularly relevant to be treated with the compositions or dosage forms described herein. Furthermore, the compositions or dosage forms described herein are thought to be relevant to other urogenital changes associated with estrogen deficiency, decreases in mucus production, changes in cell population, decreases in glycogen production, decreases in growth of lactobacilli or increases in growth of streptococci, staphylococci, or coliform bacilli. Other associated changes that are thought to be preventable by administration of the compositions or dosage forms described herein are those that may render the vagina susceptible to injury or infection, such as exudative discharges, vaginitis, and dyspareunia. Furthermore, infections of the urinary tract and incontinence are other common symptoms associated with lowered estrogen levels. Other embodiments of the invention include the prevention or alleviation of physical changes associated with estrogen deficiency, such as changes in the skin, changes in hair distribution, thickness of hair, atrophy of the breasts, or osteoporosis. The prevention and management of osteoporosis, most notably post-menopausal osteoporosis, is a particularly interesting embodiment of the invention. Furthermore, bone demineralisation, reduction of bone mass and density, thinning and interruption of trabeculae, and/or consequent increase in bone fractures or bone deformations are thought to be particularly relevant. The prophylactic treatment of osteoporosis is an interesting therapeutic application of the compositions or dosage forms of the invention. A particularly interesting embodiment of the invention is directed to lessening the frequency, persistence, duration and/or severity of hot flushes, sweating attacks, palpitations, sleep conditions, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and osteoporosis (including prevention of osteoporosis), most notably hot flushes, sweating attacks, palpitations, sleep conditions, mood changes, nervousness, anxiety, urogenital atrophy, atrophy of the breasts, as well as prevention or management of osteoporosis. Another interesting embodiment of the invention is directed to treatment of hot flushes, sweating attacks, palpitations, sleep conditions, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and osteoporosis (including prevention of osteoporosis), most notably hot flushes, sweating attacks, palpitations, sleep conditions, mood changes, nervousness, anxiety, urogenital atrophy, atrophy of the breasts, as well as prevention or management of osteoporosis.

The invention is further illustrated by the following non-limiting examples.

Materials and Methods

Determination of Decomposition Products

Separation and quantification of calcium 5-methyl-(6S)-tetrahydrofolate as well as of its degradation is conducted by HPLC on a reversed-phase column (Ph. Eur. 2.2.9, USP <621>, JP No. 27) using an external calibration standard. Samples must be analysed without delay.

| Detector: | UV detection at 280 nm |
|---|---|
| | For identity: DAD detector 210-250 nm |
| Injection volume: | 10 µl |
| Column: | Steel, length: 5 cm; Inner diameter: 4.6 mm |

-continued

| Stationary phase: | Atlantis ® C18; 3 µm or equivalent | | | |
|---|---|---|---|---|
| Temperature of column oven: | 35° C. | | | |
| Flow rate: | 2 ml/min | | | |
| Mobil phase: | A: 0.05 M $NaH_2PO_4$ adjusted to pH 3.50-3.55 with phosphoric acid | | | |
| | B: Methanol | | | |
| | C: Water | | | |
| Gradient: | Time (min) | % A (v/v) | % B (v/v) | % C(v/v) |
| | start | 99 | 1 | 0 |
| | 26 | 73 | 27 | 0 |
| | 26 | 0 | 27 | 73 |
| | 27 | 0 | 27 | 73 |
| | 27 | 0 | 90 | 10 |
| | 35 | 0 | 90 | 10 |

| Peak assignment | Comments | $t_R$ (rel) |
|---|---|---|
| ABGA | degradation product | 0.39 |
| L-MEFOX | degradation product | 0.75 |
| calcium 5-methyl-(6S)-tetrahydrofolate | active ingredient | 1 |

Dissolution

Dissolution of ethinylestradiol and drospirenone was investigated by the USP XXIX Paddle Method II using water at 37° C. as the dissolution media and 50 rpm as the stirring rate.

Dissolution of calcium 5-methyl-(6S)-tetrahydrofolate was investigated by the USP XXIX Paddle Method II using a 0.03% ascorbic acid aqueous solution (adjusted to pH 3.5 with 0.05 M phosphate buffer) at 37° C. as the dissolution media and 50 rpm as the stirring rate.

EXAMPLES

Example 1

Direct Compression; Microcrystalline Cellulose

A tablet core of 80 mg having the following composition was prepared by direct compression:

| Ingredient | Amount (mg) |
|---|---|
| Ethinylestradiol (as micronised β-cyclodextrin complex) | 0.030 |
| Micronised drospirenone | 3.000 |
| Metafolin ® | 0.451 |
| Microcrystalline cellulose (Avicel ® PH-101) | 73.319 |
| Croscarmellose sodium | 1.600 |
| Magnesium stearate | 1.600 |

The stability of calcium 5-methyl-(6S)-tetrahydrofolate upon storage under various conditions was tested. The following stability data (see Tables 1 and 2 below) were obtained upon storage at 25° C./60% RH and 40° C./75% RH, respectively. Stability was tested in open as well as closed containers.

TABLE 1

| | Sum of decomposition products in % | | | |
|---|---|---|---|---|
| Months | 25° C./ 60% RH closed | 25° C./ 60% RH open | 40° C./ 75% RH closed | 40° C./ 75% RH open |
| 0 | 2.1 | 2.1 | 2.1 | 2.1 |
| 1 | 2.4 | 2.6 | 3.0 | 7.2 |
| 3 | 2.7 | 2.6 | 3.2 | 15.0 |
| 6 | 3.2 | — | 4.2 | — |

TABLE 2

| | Amount of Metafolin ® in % | |
|---|---|---|
| Months | 25° C./60% RH closed | 40° C./75% RH closed |
| 0 | 101.2 | 101.2 |
| 1 | 103.1 | 101.2 |
| 3 | 99.2 | 96.0 |
| 6 | 99.8 | 94.3 |

Figure 1:
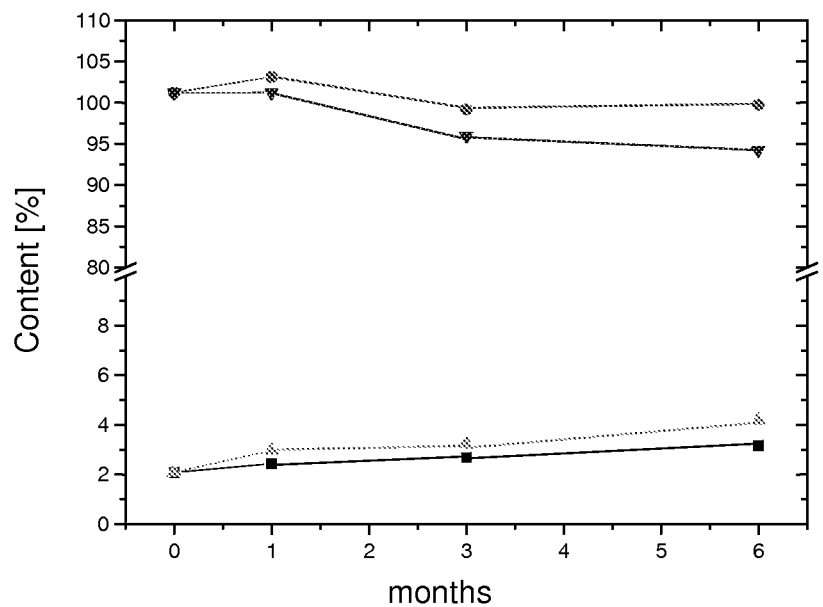
FIG. 1 shows the stability of calcium 5-methyl-(6S)-tetrahydrofolate in a tablet prepared as described in Example 1.

As can be seen, a satisfactory stability of calcium 5-methyl-(6S)-tetrahydrofolate was obtained at 25° C., even under conditions were the tablet was allowed to be exposed to open air. Furthermore, a satisfactory stability was obtained at 40° C. (closed container), whereas a significant degradation of calcium 5-methyl-(6S)-tetrahydrofolate was seen when the tablet was stored at 40° C. and, at the same time, exposed to open air. The above stability data are also depicted in FIG. 1.

The dissolution profiles are shown in FIG. 2. As can be seen from FIG. 2, ethinylestradiol and calcium 5-methyl-(6S)-tetrahydrofolate were released immediately from the tablet composition, whereas the dissolution of drospirenone was unsatisfactory slow. This finding was surprising, in particular since the tablet disintegrated within 5 minutes under the conditions used.

Example 2

Direct Compression; Cellactose® (Lactose Monohydrate/Cellulose Powder)

A tablet core of 80 mg having the following composition was prepared by direct compression:

| Ingredient | Amount (mg) |
|---|---|
| Ethinylestradiol (as micronised β-cyclodextrin complex) | 0.030 |
| Micronised drospirenone | 3.000 |
| Metafolin ® | 0.451 |
| Cellactose ® | 73.319 |
| Croscarmellose sodium | 1.600 |
| Magnesium stearate | 1.600 |

The stability of calcium 5-methyl-(6S)-tetrahydrofolate was found not to be satisfactory when stored at 25° C./60% RH and 40° C./75% RH, respectively. Like in Example 1, the dissolution of drospirenone was unsatisfactory slow.

Example 3

Direct Compression; Tablettose® (Lactose Monohydrate)

A tablet core of 80 mg having the following composition was prepared by direct compression:

| Ingredient | Amount (mg) |
| --- | --- |
| Ethinylestradiol (as micronised β-cyclodextrin complex) | 0.030 |
| Micronised drospirenone | 3.000 |
| Metafolin ® | 0.451 |
| Tablettose ® | 74.119 |
| Starch 1500 ® | 1.600 |
| Magnesium stearate | 0.800 |

Example 4

Direct Compression; Microcrystalline Cellulose/Lactose Monohydrate

In order to investigate whether the dissolution of drospirenone could be increased, it was decided to prepare a tablet according to Example 1, but where about one third of the microcrystalline cellulose was replaced by lactose monohydrate (despite lactose monohydrate's destabilising effect on calcium 5-methyl-(6S)-tetrahydrofolate, cf. Examples 2 and 3).

Thus, a tablet core of 80 mg having the following composition was prepared by direct compression:

| Ingredient | Amount (mg) |
| --- | --- |
| Ethinylestradiol (as micronised β-cyclodextrin complex) | 0.030 |
| Micronised drospirenone | 3.000 |
| Metafolin ® | 0.451 |
| Microcrystalline cellulose (Avicel ® PH-101) | 48.899 |
| Lactose monohydrate (Pharmatose ® DCL 11) | 24.420 |
| Croscarmellose sodium | 1.600 |
| Magnesium stearate | 1.600 |

A satisfactory stability of calcium 5-methyl-(6S)-tetrahydrofolate upon various storage conditions was observed.

The dissolution profile is shown in FIG. 3, and as can be seen from FIG. 3 dissolution of drospirenone was unsatisfactory slow and almost identical to the release profile obtained for the tablet prepared in Example 1.

Example 5

Fluidised Bed Granulation; Microcrystalline Cellulose/Lactose Monohydrate

A tablet core of 80 mg having the following composition was prepared

| Ingredient | Amount (mg) |
| --- | --- |
| Ethinylestradiol (as micronised β-cyclodextrin complex) | 0.020 |
| Micronised drospirenone | 3.000 |
| Metafolin ® | 0.451 |
| Microcrystalline cellulose (Avicel ® PH 101) | 24.800 |
| Lactose monohydrate, crystalline | 45.319 |
| HPC, viscosity 5 | 1.600 |
| Croscarmellose sodium | 3.200 |
| Magnesium stearate | 1.600 |

A granulate preparation was prepared by charging a fluidised bed granulator with drospirenone, ethinylestradiol, lactose monohydrate, microcrystalline cellulose and activating the fluidised bed. An aqueous solution of binder (HPC) was sprayed continuously onto the fluidised bed while drying by heating the air stream of the fluidised bed. At the end of the process, calcium 5-methyl-(6S)-tetrahydrofolate, crosscarmellose and magnesium stearate were sucked into the granulator and mixed with the granules by maintaining the fluidised bed. The resulting granulates were compressed into tablet cores using a tablet press.

A satisfactory stability of calcium 5-methyl-(6S)-tetrahydrofolate upon various storage conditions was observed.

Furthermore, and as can be seen from FIG. 3, an immediate-release profile of drospirenone was observed, i.e. the dissolution of drospirenone was comparable to the dissolution profile of the dropirenone-containing oral contraceptive Yasmin®.

Example 6

Fluidised Bed Granulation; Microcrystalline Cellulose

A tablet core of 80 mg having the following composition was prepared

| Ingredient | Amount (mg) |
| --- | --- |
| Ethinylestradiol (as micronised β-cyclodextrin complex) | 0.030 |
| Micronised drospirenone | 3.000 |
| Metafolin ® | 0.451 |
| Microcrystalline cellulose (Avicel ® PH 101) | 71.719 |
| HPC, viscosity 5 | 1.600 |
| Croscarmellose sodium | 1.600 |
| Magnesium stearate | 1.600 |

A granulate preparation was prepared by as described in Example 5. A satisfactory stability of calcium 5-methyl-(6S)-tetrahydrofolate upon various storage conditions was observed.

As can be seen from FIG. 3, drospirenone was released slower from this tablet compared to the tablet prepared in Example 5. However, the drospirenone-release was still satisfactory and comparable to the dropirenone-containing oral contraceptive Yaz®.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of U.S. Provisional Application 60/818,512 filed Jul. 6, 2006, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A tablet core comprising a solid pharmaceutical composition comprising,
particles comprising 3 mg of micronized drospirenone, 0.02 or 0.03 mg of ethinyl estradiol, 25-36 wt % (based on tablet core total weight) of microcrystalline cellulose, 52-63 wt % (based on tablet core total weight) of lactose monohydrate, and 0.42-0.49 mg of an alkaline earth metal salt of 5-methyl-(6S)-tetrahydrofolic acid,
wherein the in vitro dissolutions of drospirenone and the salt of 5-methyl-(6S)-tetrahydrofolic acid individually are such that at least 85% of each is dissolved from the composition within 30 minutes, as determined by the USP XXIX Paddle Method II using water (for drospirenone) and a 0.03% ascorbic acid aqueous solution (adjusted to pH 3.5 with 0.05 M phosphate buffer (for the salt of 5-methyl-(6S)-tetrahydrofolic acid) at 37° C. as the dissolution media and 50 rpm as the stirring rate, and
wherein the stability of the salt of 5-methyl-(6S)-tetrahydrofolic acid is such that at least 90% of said amount thereof is present in the composition after storage in a closed container for 12 months at 25° C. and 60% relative humidity.

2. The tablet according to claim 1, wherein the ethinyl estradiol is in the form of an estrogen-β-cyclodextrin complex.

3. The tablet according to claim 1, wherein the ethinyl estradiol is micronized.

4. The tablet according to claim 1, wherein the estrogen-β-cyclodextrin complex is micronized.

5. The tablet according to claim 1, wherein the salt of 5-methyl-(6S)-tetrahydrofolic acid is the calcium salt.

6. The tablet according to claim 5, wherein the calcium salt of 5-methyl-(6S)-tetrahydrofolic acid is in crystalline form.

7. The tablet according to claim 6, wherein the crystalline form is the Type I crystalline form.

8. The tablet according to claim 1, wherein the composition does not contain vitamin B12.

9. The tablet according to claim 1, wherein the composition contains less than 2% polyvinylpyrrolidone (PVP) by weight of the composition.

10. The tablet according to claim 1, wherein the tablet is coated.

11. The tablet according to claim 10, wherein the tablet is film-coated.

* * * * *

UNITED STATES PATENT AND TRADEMARK OFFICE
CERTIFICATE OF CORRECTION

| | |
|---|---|
| PATENT NO. | : 8,617,597 B2 |
| APPLICATION NO. | : 11/773689 |
| DATED | : December 31, 2013 |
| INVENTOR(S) | : King |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1270 days.

Signed and Sealed this
Fifth Day of May, 2015

Michelle K. Lee
*Director of the United States Patent and Trademark Office*